(12) United States Patent
Blomström et al.

(10) Patent No.: US 11,950,989 B2
(45) Date of Patent: Apr. 9, 2024

(54) DISPOSABLE HYGIENE ARTICLE

(71) Applicant: Essity Hygiene and Health Aktiebolag, Gothenburg (SE)

(72) Inventors: Philip Blomström, Gothenburg (SE); Shadi Ståhl, Mölndal (SE); Anna Bagger-Sjöbäck, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 623 days.

(21) Appl. No.: 16/640,535

(22) PCT Filed: Aug. 22, 2017

(86) PCT No.: PCT/SE2017/050839
§ 371 (c)(1),
(2) Date: Feb. 20, 2020

(87) PCT Pub. No.: WO2019/039976
PCT Pub. Date: Feb. 28, 2019

(65) Prior Publication Data
US 2020/0352797 A1    Nov. 12, 2020

(51) Int. Cl.
*A61F 13/475* (2006.01)
*A61F 13/56* (2006.01)
*A61F 13/53* (2006.01)

(52) U.S. Cl.
CPC ...... *A61F 13/4753* (2013.01); *A61F 13/5616* (2013.01); *A61F 2013/530481* (2013.01)

(58) Field of Classification Search
CPC .............. A61F 13/4753; A61F 13/5616; A61F 2013/530481; A61F 13/4704; A61F 13/4752; A61F 13/475
See application file for complete search history.

(56) References Cited

U.S. PATENT DOCUMENTS 5,387,210 A    2/1995    Murakami
5,649,917 A    7/1997    Roberts et al.
(Continued)

FOREIGN PATENT DOCUMENTS

| CL | 200902121 | 11/2009 |
|---|---|---|
| CN | 1244381 A | 2/2000 |

(Continued)

OTHER PUBLICATIONS

Pinzon Pinzon & Asociados, Third Party Submission in Application No. NC2020/0001993 dated May 5, 2019, 35 pages (with English translation).
(Continued)

*Primary Examiner* — George R Koch
*Assistant Examiner* — Christopher C Caillouet
(74) *Attorney, Agent, or Firm* — CANTOR COLBURN LLP

(57) ABSTRACT

Disposable hygiene article comprising a liquid-permeable topsheet, a liquid-impermeable backsheet and an absorbent core, flexible side flaps arranged on opposite sides of the absorbent core for attaching the article to a garment, and liquid side barriers arranged substantially along longitudinal edges of the absorbent core. The flexible side flaps each comprise at least a side layer which is secured to the topsheet by means of a seam, the seam partitioning the side layer in a first part and a second part with the first part extending from the seam towards the longitudinal centre axis and the second part extending from the seam away from said longitudinal centre axis. The first parts form the liquid side barriers.

16 Claims, 3 Drawing Sheets

(56) References Cited

U.S. PATENT DOCUMENTS

| | | | |
|---|---|---|---|
| 5,713,885 | A | 2/1998 | Jorgenson et al. |
| 6,616,644 | B1* | 9/2003 | Mizutani ............. A61F 13/4756 604/385.04 |
| 6,632,208 | B1* | 10/2003 | Mizutani ............. A61F 13/4702 604/385.04 |
| 2003/0120244 | A1 | 6/2003 | Johnson |
| 2004/0243087 | A1 | 12/2004 | Kinoshita et al. |
| 2006/0116653 | A1 | 6/2006 | Munakata et al. |
| 2009/0240225 | A1* | 9/2009 | Noda ................. A61F 13/5616 604/378 |
| 2010/0191209 | A1 | 7/2010 | Nomoto et al. |
| 2012/0323206 | A1 | 12/2012 | Mcmorrow et al. |
| 2014/0343525 | A1 | 11/2014 | Roh et al. |
| 2015/0080830 | A1 | 3/2015 | Miura |

FOREIGN PATENT DOCUMENTS

| | | |
|---|---|---|
| CN | 101448475 B | 7/2012 |
| CN | 101686881 B | 3/2013 |
| CO | 7170144 A2 | 1/2015 |
| EP | 0581258 A1 | 2/1994 |
| EP | 0940133 A2 | 9/1999 |
| EP | 1208824 B1 | 8/2005 |
| EP | 1842512 A1 | 10/2007 |
| EP | 2163229 A1 | 3/2010 |
| EP | 2281537 A1 | 2/2011 |
| ES | 2086778 T3 | 7/1996 |
| GB | 2306888 A | 5/1997 |
| JP | 2001149410 A | 6/2001 |
| JP | 2008148819 A | 7/2008 |
| JP | 4859596 B2 | 1/2012 |
| WO | 9720533 A1 | 6/1997 |
| WO | 0228334 A1 | 4/2002 |
| WO | 2007069965 A1 | 6/2007 |
| WO | 2016068957 A1 | 5/2016 |

OTHER PUBLICATIONS

National Intellectual Property Administration (CNIPA) of the People's Republic of China, 2nd Office Action issued in CN Application No. 201780093240.2, dated Oct. 15, 2021 with English translation, 17 pages.
Australian Government, IP Australia, Examination report No. 1 for standard patent application issued in Australian Patent Application No. 2017428323, dated Aug. 4, 2020, 4 pages.
Federal Service for Intellectual Property, Russia, Official Notification of examination results and Search Report issued in Application No. 2020111223(018873), dated Aug. 11, 2020, 11 pages, with English translation.
Pinzon Pinzon & Asociados, Third Party Submission in Application No. NC2020/0001993 dated May 5, 2019, 19 pages (no English translation available).
Australian Government, IP Australia, Examination report No. 1 for standard patent application issued in corresponding Australian Application No. 2017428325, dated Aug. 6, 2020, 5 pages.
Federal Service for Intellectual Property, Russia, Official Action and Search Report issued in corresponding Russian Patent Application No. 2020111224/03(018874), dated Aug. 11, 2020, 13 pages, with English Translation.
International Search Report and Written Opinion for International Application No. PCT/SE2017/050839, dated Apr. 11, 2018, 10 pages.
International Search Report and Written Opinion for International Application No. PCT/SE2017/050840, dated Apr. 11, 2018, 14 pages.
International Search Report and Written Opinion for International Application No. PCT/SE2017/050841, dated Apr. 11, 2018, 12 pages.
European Patent Office, Extended European Search Report issued in EP Application No. 17922685.7-1102, dated Mar. 11, 2021, 6 pages.
National Intellectual Property Administration (CNIPA) of the People's Republic of China, Office Action issued in CN Application No. 201780093240.2, dated Mar. 26, 2021 with English translation, 17 pages.
Colombian Office Action; Colombian Application No. NC2020/0001993; dated Sep. 30, 2022; 20 pages with translation.
Egyptian Office Action; Egyptian Application No. 2020020254; 8 pages with translation.
Colombian Office Action; Colombian Application No. NC2020/0001993; dated Jun. 5, 2023 (25 pages; with translation).
Egyptian Office Action for Egyptian Counter-Part Application to International Application No. PCT/SE2017/050839; International Filing Date Aug. 22, 2017; dated May 31, 2023 (5 Pages).

* cited by examiner

DISPOSABLE HYGIENE ARTICLE

CROSS REFERENCE TO RELATED APPLICATIONS

This is a U.S. National Phase application of PCT/SE2017/050839, filed Aug. 22, 2017, the disclosure of which is incorporated herein by reference in its entirety for all purposes.

TECHNICAL FIELD

The present disclosure relates to disposable hygiene articles, such as adult incontinence articles, sanitary towels and panty liners or the like having flexible side flaps and provided with liquid side barriers.

BACKGROUND

Disposable hygiene articles have to meet high requirements. They should for example be discreet, soft and comfortable to wear and at the same time they should have a reliable security against leakage. Such disposable hygiene articles usually comprise a liquid-permeable topsheet, a liquid-impermeable backsheet and an absorbent core arranged between the topsheet and the backsheet.

During the use of disposable hygiene articles there is a risk that bodily discharges such as urine, menstrual fluids or other bodily fluids move on top of the liquid-permeable topsheet and leak past the edges of the article. Although liquid movements can take place in any direction for example in the longitudinal direction or in the transverse direction of the hygiene article, liquid movement in transverse direction of the hygiene article is particularly worrying because only a relatively small liquid movement in the transverse direction may cause the liquid to leak outside the longitudinal side edges of the hygiene article with the result that surrounding articles such as clothing, bedclothes, seat cushions are soiled by discharged liquid. The risk of so-called side-edge leakage is the highest during night, for example when sleeping on the side.

Many different attempts have been made to reduce or eliminate the problem of side-edge leakage.

Some known hygiene articles are provided with side flaps, also referred to as wings, projecting outwardly from the hygiene article. When fitting the article for wear, these side flaps are intended to be folded around the edges of the leg openings of the wearer's underpants and to be fastened to the outside thereof.

Some known hygiene articles are provided with liquid side barriers along the longitudinal edges of the absorbent core, with elastic threads provided in or on the material to raise the liquid side barriers in use. Such solutions require additional material and additional process steps, making such hygiene articles technically complex.

SUMMARY

It is an aim of the present disclosure to provide a disposable hygiene article provided with liquid side barriers which is technically less complex.

It is another aim of the present disclosure to provide a disposable hygiene article with reduced risk of side-edge leakage without considerable increase of the amount of material used.

It is a further aim of the present disclosure to provide a disposable hygiene article provided with liquid side barriers that can be manufactured in a relatively simple manufacturing process.

At least one of the above aims may be achieved by a disposable hygiene article as defined in the independent claim.

According to an aspect of the present disclosure, a disposable hygiene article is provided, comprising a liquid-permeable topsheet, a liquid-impermeable backsheet and an absorbent core arranged between said topsheet and said backsheet, the absorbent core defining a longitudinal centre axis which extends substantially in the middle of the core in longitudinal direction L of the article. The disposable hygiene article is adapted to be releasably attached to a garment, such as underpants or briefs. In use of the article the topsheet is facing the crotch area of a user and the backsheet is facing away from the crotch area of the user.

The article further comprises flexible side flaps arranged on opposite sides of said absorbent core and provided for attaching the article to the garment, and liquid side barriers arranged substantially along longitudinal edges of said absorbent core and provided to reduce or minimize side-edge leakage. The flexible side flaps each comprise at least a side layer which is secured to said topsheet by means of a seam, said seam partitioning said side layer in a first part and a second part with said first part extending from said seam towards said longitudinal centre axis and said second part extending from said seam away from said longitudinal centre axis. Each said first part extends above said topsheet and is loose therefrom to form one of the liquid side barriers.

It has been found that the first parts of the side layers of the flexible side flaps, which extend above a part of the topsheet, in particular above longitudinal edge portions thereof, while being loose therefrom, can function very well as liquid side barriers. Without being bound by theory, it is believed that the effect may be achieved by the fact that liquid which flows sideways along the topsheet finds a barrier in its path as a result of the seam and the first part of the side layer on that side, even when it lies on top of the topsheet. The construction of the article of the present disclosure may thus be simplified, since the need for elastic elements for raising the side barriers may be avoided.

In embodiments according to the present disclosure, the liquid side barriers may be provided for being at least partly raised to a substantially upright position in use. The raising of at least part of the side barriers in use may enhance the barrier and thus further reduce side-edge leakage.

In embodiments according to the present disclosure, the liquid said side barriers may be provided for being at least partly raised by folding said flexible side flaps to a position in which said hygiene article is secured to said garment. The raising of at least part of the side barriers can in this way be ensured even without provision of elastic elements to raise the side barriers.

In embodiments according to the present disclosure, the side barriers may be provided for being at least partly raised by folding said flexible side flaps substantially along said seams. This can further ensure a substantially upright position of the side barriers in use.

In embodiments according to the present disclosure, the flexible side flaps may each comprise a side portion of said backsheet, i.e. in this embodiment the side flaps comprise the side layer and a side portion of the backsheet above each other. In certain embodiments, the side layer and the side portion may be preferably attached to each other, preferably along their outer edges. The attachment of these layers to each other may have the effect that upon folding of the side flaps, in certain embodiments, preferably along or in the vicinity of the seams, tension is created which assists in raising the side barriers to a suitable substantially upright position.

In embodiments according to the present disclosure, the first part of each of said side layers is formed by a multiple layered section of the respective side layer, which is preferably formed by at least one fold of said side layer. Such a multi-layer construction may strengthen the liquid side barrier and further reduce side-edge leakage.

In embodiments according to the present disclosure, the first parts, which form the side barriers, may extend over the full length of the article.

In embodiments according to the present disclosure, the first parts have a width in transverse direction T of the article ranging from 2.0 to 10.0 mm, preferably from 3.0 to 7.0 mm.

In embodiments according to the present disclosure, the liquid side barriers may consist entirely of or comprise non-elastic material, i.e. the need for elastic elements to ensure proper raising of the side barriers in use may be avoided.

In embodiments according to the present disclosure, the article may further comprise an acquisition layer positioned between said absorbent core and said topsheet.

In embodiments according to the present disclosure, the seam may be obtained by welding, such as ultrasonic welding, by applying a chemical compound such as an adhesive, by applying heat and/or pressure.

In embodiments according to the present disclosure, a coloured indication may be provided on the article to highlight the presence of the liquid side barriers, said coloured indication preferably being provided by a print on the topsheet underneath each of said first parts, said print preferably being provided on a garment facing side of the topsheet. It has been found that such highlighting of the presence of the side barriers may signal an increased leak protection, and thus give an increased sense of security.

BRIEF DESCRIPTION OF THE DRAWINGS

The present disclosure will be discussed in more detail below, with reference to the attached drawings, in which.

DETAILED DESCRIPTION OF PARTICULAR EMBODIMENTS

Figure 1:
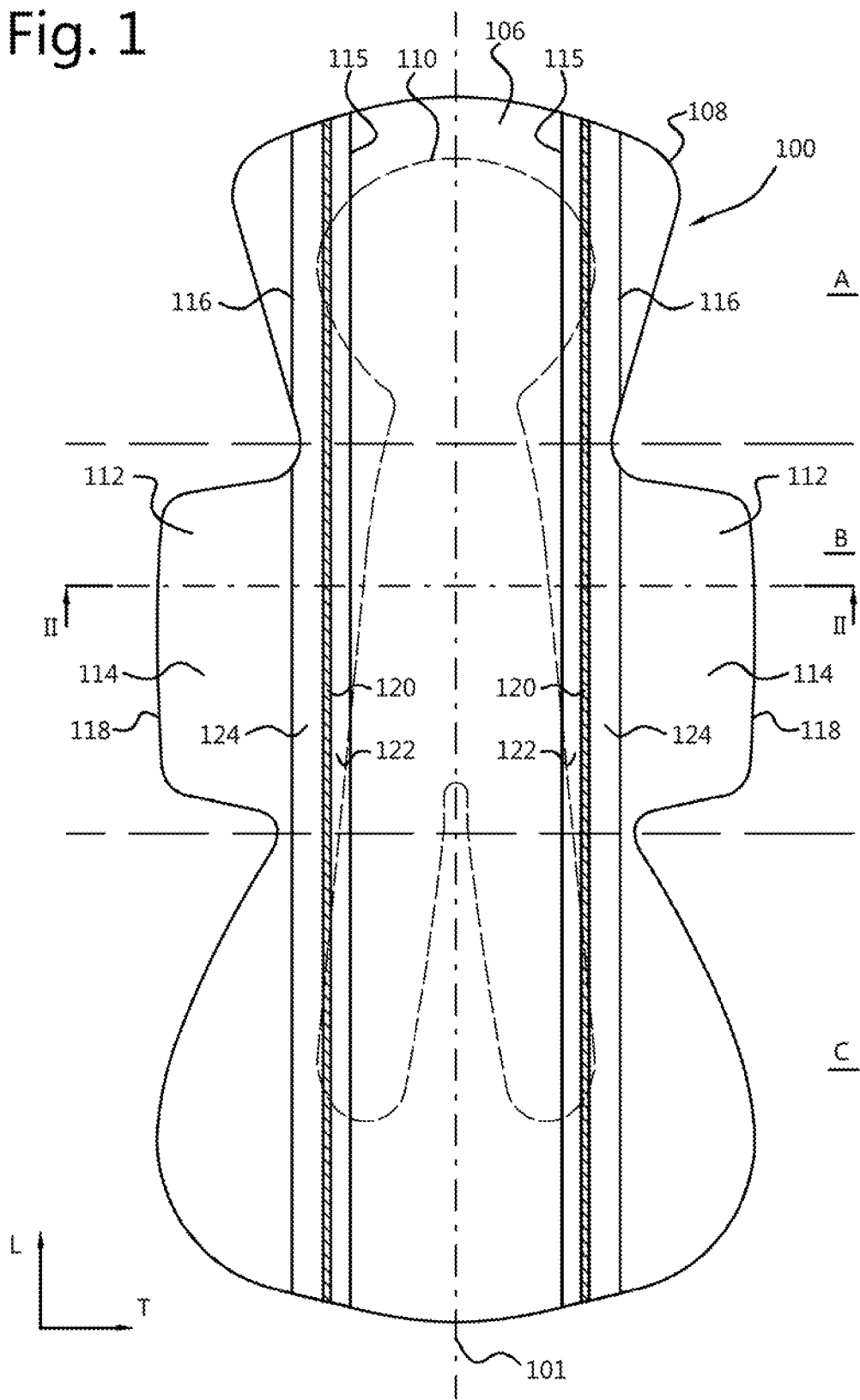
FIG. 1 shows a top view of a first embodiment of a disposable hygiene article according to the present disclosure.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

Disposable hygiene articles are absorbent articles aimed for personal hygiene and are arranged to absorb body exudate, such as blood or urine. Such disposable hygiene articles are single-use articles and comprise for example adult incontinence articles, sanitary towels and panty liners.

Generally, the disposable hygiene articles are releasably attachable on a garment, suitably an undergarment of a user, by means of an adhesive material. A first embodiment is described with reference to FIGS. 1 and 2.

The article 100 has a "body facing side" intended to face the body of the user, in particular to face the body in the crotch area of the user when the article is worn, and a "garment facing side" intended to face the garment, in particular the undergarment or briefs when the article is worn. FIG. 1 shows a view onto the article 100 from the body facing side.

The article 100 has a longitudinal direction L and a transverse direction T and has a longitudinal centre axis 101 which extends substantially in the middle of the absorbent part of the article. The article may be generally symmetrical with respect to this longitudinal centre axis, though this is not essential.

The article may comprise a front portion A, a middle portion B and a rear portion C in the longitudinal direction of the article. The front and rear portions A, C may be shaped to assist the user in optimally positioning the article 100 in their garment. The article 100 may be adapted for being folded for example in three with the front and rear portions A, C folded over the middle portion B when the article is individually packaged for delivery to a consumer. The article may be individually packaged by for example wrapping a thin plastic material around the article.

The disposable hygiene article 100 comprises a liquid-permeable topsheet 106, a liquid-impermeable backsheet 108 and an absorbent core 110, in an embodiment, preferably comprising an absorbent material. The liquid-permeable topsheet 106 is arranged at the body facing side of the article and is intended to be in contact with the body of the user, in particular with the crotch area of the user. The liquid-impermeable backsheet 108 is arranged at the garment facing side of the article and is intended to be in contact with the garment. The absorbent core 110 is arranged between and, in an embodiment, preferably enclosed by the topsheet 106 and the backsheet 108. By liquid-permeable is meant that liquid, such as urine, blood or water, can pass through the material. By liquid-impermeable is meant that liquid, such as urine, blood or water, substantially cannot pass through the material. By absorbent material is meant material that is capable of absorbing or soaking up liquid, such as urine, blood or water.

Figure 5:
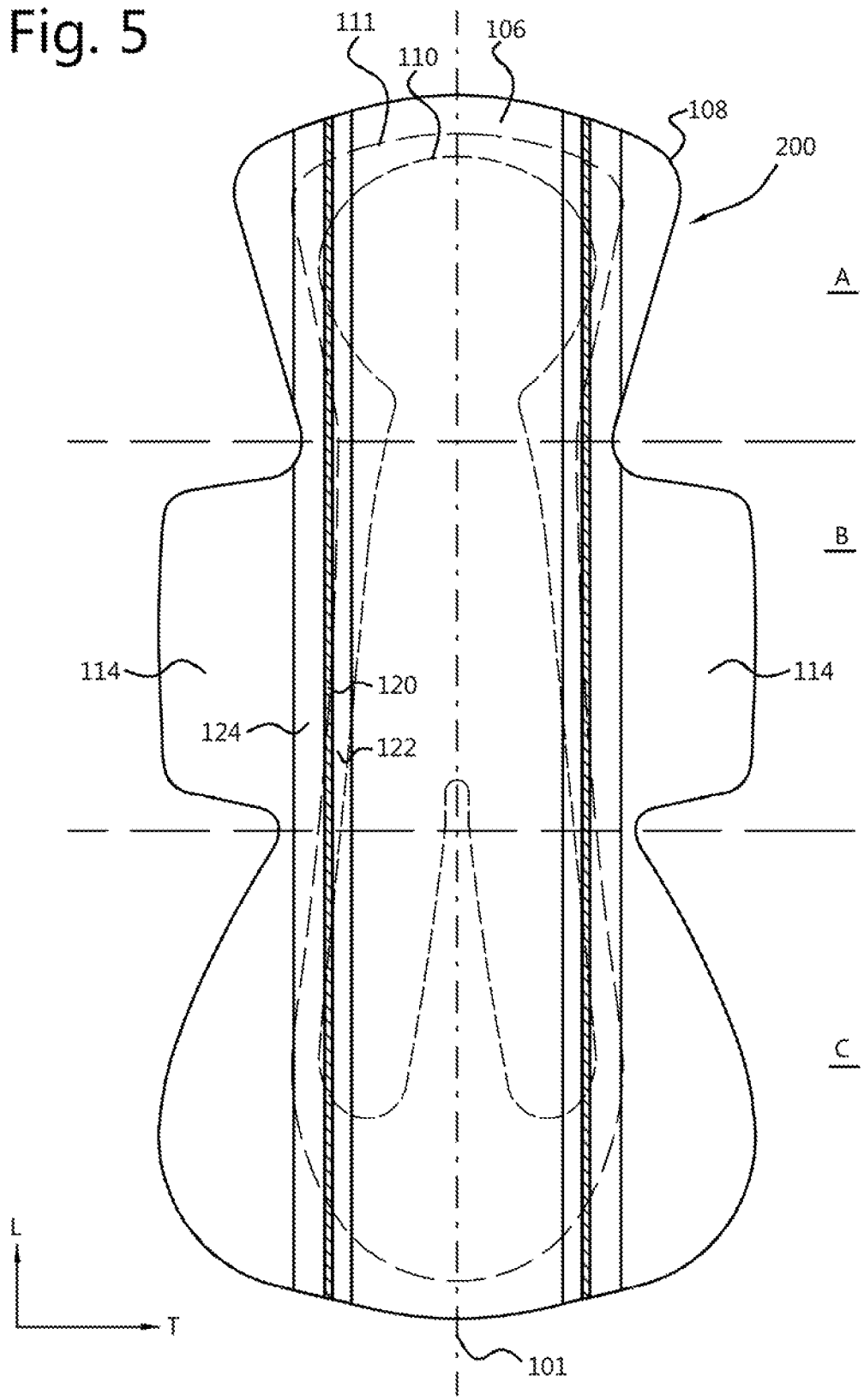
FIG. 5 shows a top view of a third embodiment of a disposable hygiene article according to the present disclosure.

The article 100 may comprise further layers or sheets, such as an acquisition layer 111 (see FIG. 5). In certain embodiments, an acquisition layer may be preferably located beneath the topsheet 106, and may be more preferably in contact with the garment facing side (i.e. the side facing the core 110) of the topsheet. The acquisition layer is intended to quickly absorb liquid and to spread the liquid before it is transported to the absorbent core, where it is retained. In an embodiment, the acquisition layer preferably may be comprises of an air-laid layer or wadding. The acquisition layer can be joined with the topsheet. The topsheet and the optional acquisition layer may be attached together by embossing, by using an adhesive or by means of ultrasonic processing to form a laminate. If the layers are attached together by means of ultrasonic processing, at least one of the topsheet or acquisition sheet comprises a thermoplastic material.

The other layers or sheets of the article 100 may be laminated together or the other layers may be attached together by means of embossing or adhesive. When laminated together the sheets are joined by means of a reinforcement executed with ultrasonic processing essentially along the peripheral edge of the sheets that forms an edge seal of the laminate so that the risk of any leakage and spread of liquid via the peripheral edge is minimized or eliminated. The reinforcement can extend from the periphery and towards the inside of the article for a distance of about 2-6 mm.

The topsheet 106 usually includes regenerated cellulose fibers, polyester or other synthetic polymer fibers, or films and is provided on the body facing side of the hygiene article. The topsheet is provided for comfort and conformability and for directing the liquid to the underlying absorbent core. In an embodiment, the liquid-permeable topsheet 106 is preferably manufactured from a material that exhibits characteristics such as dryness and softness during the time when the absorbent article is being worn, because the topsheet 106 is in contact with the user's body. It is also desirable for the topsheet 106 to have a soft and textile-like surface which remains dry, even in the event of repeated wetting. The topsheet 106 can consist of or comprise a nonwoven material, for example, with a soft and smooth surface, such as a spunbond material made from polypropylene fibres. A perforated, hydrophobic nonwoven material may be used in order to permit the surface that is closest to the user's body to be kept dry, in conjunction with which openings are formed in the material that are larger than the holes between the fibres in the material. In this way, liquid can be led down through the perforated openings in the topsheet to the subjacent absorbent core. Other examples of materials for the topsheet are perforated plastic films such as a perforated polyester film attached to a nonwoven sheet. The topsheet may also be manufactured from a spunbond nonwoven material, an air-through nonwoven material, a spunlace nonwoven (hydroentangled) material, a meltblown nonwoven material, or a combination of these, such as a SMS-material, which is a layered product including spunbond-meltblown-spunbond nonwoven materials. The raw material can be polypropylene (PP), polyethylene (PE) polyester (PET), polyamide (PA), or a combination of these. If a combination is used, this can be a mixture of fibres from different polymers, although each fibre can also include different polymers (e.g. PP/PE bi-component fibres or PP/PE copolymers). Where appropriate, the plastic film can consist of PE or PP, PET, PLA or amyl (or, for that matter, any other thermoplastic polymer), or a mixture or copolymers of the aforementioned polymers. In an embodiment, the topsheet preferably comprises a spunbond material comprising polypropylene fibres which provide for optimal comfort and handleability of the article. Other suitable fibres for making the nonwoven material are for example natural fibres such as bamboo, cotton and flax.

In the embodiment shown in FIG. 1, the absorbent core 110 has a specific shape, however the absorbent core 110 may also have another shape, for example a simpler shape like rectangular or oval. The absorbent core 110 may be manufactured from a fibre material in the form of natural or synthetic fibres with absorbent characteristics, or a mixture of natural fibres and synthetic fibres or other absorbent materials of a previously disclosed kind that are suitable for use in, for example, sanitary towels, incontinence pads and panty liners. The absorbent core may comprise one or more layers of defibrillated cellulosic fibres, for example cellulose fluff pulp. Other materials, which may be used, are for example absorbing or wettable nonwoven materials, foam materials or synthetic fibre materials.

The absorbent core 110 may comprise superabsorbent materials or may be free of superabsorbent material. In case the absorbent core comprises superabsorbent materials, the amount of superabsorbent materials ranges preferably between 1% and 30% by weight of the absorbent core in certain embodiments. The superabsorbent material may be polymeric materials in the form of particles, fibres, flakes or the like, and the material possesses the ability to absorb and chemically bind liquid equivalent to several times their own weight to form an aqueous gel. This imparts a very high liquid-absorbent capacity to the finished hygiene article while the article is still soft and easy to handle and manufacture.

Different layers of the article 100 may be laminated together or may be attached together for example by means of embossing or by means of an adhesive. The side layers 112 are for example laminated or attached to the backsheet, for example by means of embossing or by means of an adhesive.

Figure 2:
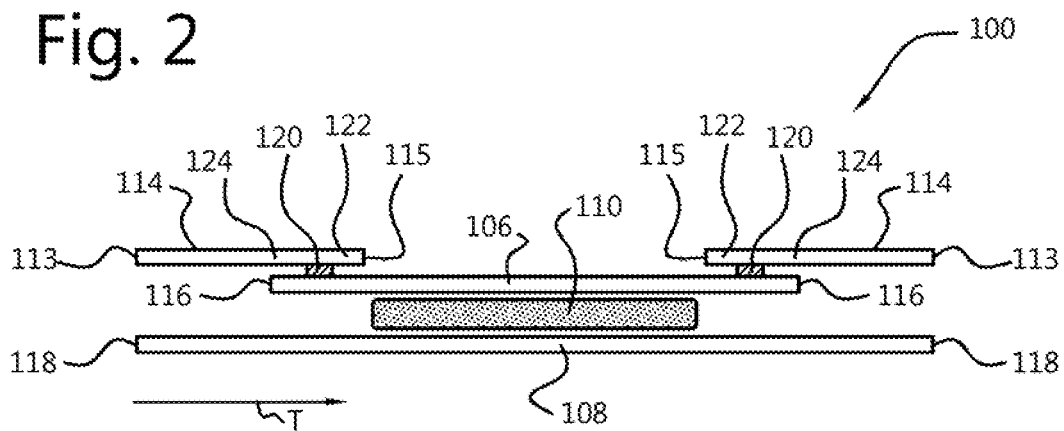
FIG. 2 is a cross-sectional (exploded) view of the article along the line II-II shown in FIG. 1.

In the embodiment shown in FIGS. 1 and 2, the topsheet 106 extends transversally, i.e. in the transverse direction T, from the longitudinal centre axis 101 beyond the edges of the absorbent core 110 (i.e. beyond the longitudinal side edges of the absorbent core 110) up to longitudinal side edges 116.

In the embodiment shown in FIGS. 1 and 2, the backsheet 108 extends transversally, i.e. in the transverse direction T, from the longitudinal centre axis 101 beyond the longitudinal side edges 116 of the topsheet 106. Preferably, at least in the middle portion B of the article 100, the backsheet 108 extends up to longitudinal side edges 118, so that the backsheet 108 has side portions which form a bottom layer of the flexible side flaps 112 on either side of the absorbent core 110. In the embodiment shown, the backsheet 108 also extends beyond the longitudinal side edges 116 of the topsheet 106 in the front and rear parts A and C, but this can be carried out differently.

In alternative embodiments, the longitudinal side edges 116 and 118 of the topsheet 106 and the backsheet 108 could coincide in the front part A and/or the rear part C and/or even in the middle part. In the latter case, the side flaps 112 may be formed by a single layer, namely the side layer 114 described herein, or by a combination of this side layer 114 and another layer.

In the embodiment shown in FIGS. 1 and 2, the flexible side flaps 112 comprise the side portions of the backsheet 108 and, on each side, a side layer 114. This side layer 114 extends transversally from an inner longitudinal edge 115 up to an outer longitudinal edge 113. The inner longitudinal edge 115 is, on each side, located between the longitudinal side edge 116 of the topsheet 106 and the centre axis 101, preferably closer to the longitudinal side edge 116 so as to cover only an edge portion of the absorbent part of the article. The side layer 114 may be attached to the topsheet 106 by means of a seam 120. This seam 120 partitions the side layer 114 in a first part 122 and a second part 124 with said first part 122 extending from the seam 120 towards the longitudinal centre axis 101 up to the inner longitudinal edge 115 and said second part 124 extending from the seam 120 away from the longitudinal centre axis 101 up to the outer longitudinal edge 113. The first part 122 extends above the topsheet 106 and is loose therefrom at least in the middle portion B of the article 100 and in use forms a liquid side barrier on the respective side of the absorbent part of the article.

In the embodiment shown in FIGS. 1 and 2, the seam 120 is located substantially in the middle of the area of overlap of the side layer 114 and the topsheet 106, i.e. substantially in the middle between the respective edges 115 and 116. In other embodiments, the seam may be located closer towards the one edge or the other. The first part 122, forming the liquid side barrier in use, preferably has a length, measured in transverse direction T, of 2.0 to 10.0 mm, preferably 3.0 to 7.0 mm.

In the embodiment shown in FIGS. 1 and 2, the topsheet has longitudinal edge portions 107 which may be provided with coloured indications to indicate or highlight the presence of the liquid side barriers 122 to the user. This coloured indication may be printed on the topsheet 106 underneath each of said first parts 122, possibly throughout the areas of overlap between the respective edges 115 and 116. This print may be provided on the garment facing side of the topsheet 106, possibly in the same process step as a further coloured indication which is applied in the middle part of the topsheet 106 (where the absorbent core 110 is located). The topsheet is, due to its liquid permeability, a layer of translucent material, and preferably also the side layer 114 is made of a translucent material. The at least one layer which is/are located above the coloured indications are translucent in such a way that the coloured indications are to some extent visible to the user through said layer(s).

In the embodiment shown, the side layer 114 is also present in the front and rear parts A and C, i.e. the seam 120 is a longitudinal seam extending over the full length of the article 100 in the longitudinal direction L. However, this is not essential.

The seam 120 can be obtained by any technique suitable to secure the side layer 114 to the topsheet 106 for example by welding, such as ultrasonic welding, by applying a chemical compound such as an adhesive, by applying heat and/or pressure.

In the embodiment shown, the outer longitudinal edge 113 of the side layer 114 coincides with the longitudinal side edge 118 of the backsheet 108 and these two layers are attached to each other along these edges 113, 118. This is preferred as this may simplify the manufacturing process (simultaneous cutting and attachment step), but is not essential.

The side flaps 112, which in the embodiment shown in FIGS. 1 and 2 comprise the side layers 114 and the side portions of the backsheet 108 attached to each other, are configured for being folded about the garment to secure the position of the hygiene article 100 with respect to the garment. To this end, the flexible side flaps 112 may be suitably provided with a pressure sensitive adhesive provided on the garment facing side of the backsheet 108. Such adhesive, to secure the position of the article to the garment during use, may also be provided on the garment facing side of the backsheet 108 underneath the absorbent part of the article.

Figure 4:
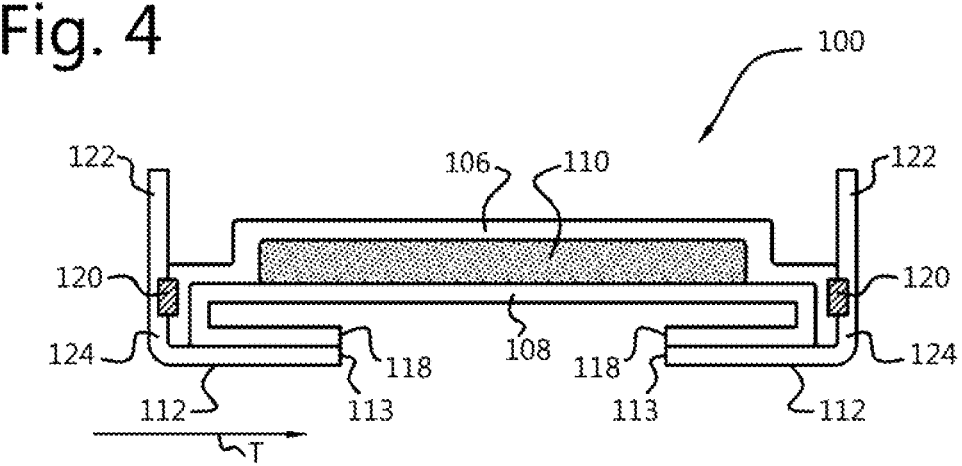
FIG. 4 is a cross-sectional view of the article of FIGS. 1 and 2 while in use.

Upon folding the side flaps 112 as intended, i.e. substantially along the seam 120 as shown in FIG. 4, the first parts 122 are raised to a substantially upright position. The substantially upright position of these first parts 122 may enhance the functioning as barrier for the liquid. The movement to the substantially upright position may result from tension which is created by folding the side flaps and it is thus not needed to provide elastic elements in or on the material of the side layers 114 to achieve said movement.

Figure 3:
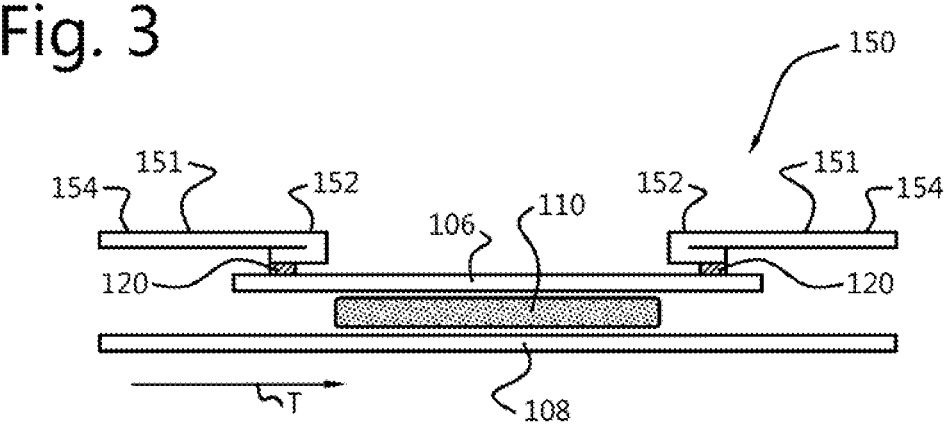
FIG. 3 is a cross-sectional (exploded) view of a second embodiment of a disposable hygiene article according to the present disclosure.

FIG. 3 shows an alternative embodiment of a disposable hygiene article 150 according to the present disclosure. This embodiment is in many aspects the same as that of FIGS. 1 and 2 and like parts are indicated with like reference numbers, so only the differences will be discussed here. In this embodiment, the side flaps comprise, on each side, a side portion of the backsheet 108 and a side layer 151 which is partitioned by the seam 120 into a first part 152 and a second part 154. In this embodiment, the first part 152 is a folded part of the side layer 151, such that the first part 152 comprises two layers of the material, which may create a stronger side barrier in use. In alternative embodiments, the folded part may also extend further, i.e. outwards beyond the seam 120, or the side layer may be entirely formed by a two layers of the material, folded at the inner longitudinal edge, or the side layer 151 may be folded multiple times to create a multi-layer side barrier 152, for example a Z-folded part.

FIG. 5 shows another embodiment of a disposable hygiene article 200 according to the present disclosure. This embodiment is in many aspects the same as that of FIGS. 1 and 2 and like parts are indicated with like reference numbers. A difference is that the article 200 comprises an acquisition layer 111, as described elsewhere herein, located in between the topsheet 106 and the core 110.

In all embodiments, the side layers 114, 151 may comprise a hydrophobic material to further reduce the risk of side-edge leakage, although this is not essential. The side layers may for example comprise a hydrophobic non-woven material or a hydrophobic spunbond material. Furthermore a hydrophobic coating layer can be applied on the material of the side layer or the material of the side layer can be treated for example with surfactants to adjust its degree of hydrophilicity.

The invention claimed is:

1. A disposable hygiene article, comprising:
   a liquid-permeable topsheet, a liquid-impermeable backsheet and an absorbent core arranged between said topsheet and said backsheet, said absorbent core defining a longitudinal centre axis which extends substantially in the middle of said core in a longitudinal direction (L) of the article;
   flexible side flaps arranged on opposite sides of said absorbent core and provided for attaching said article to a garment; and
   liquid side barriers arranged substantially along longitudinal edges of said absorbent core and provided to reduce side-edge leakage;
   wherein said flexible side flaps each comprise a side portion of the backsheet and a side layer which is secured to said topsheet by means of a seam, said seam being located at a portion of said side layer in overlapping arrangement with said topsheet, said seam being at a position offset from an inner longitudinal edge of said side layer and offset from a longitudinal side edge of said topsheet, said seam partitioning said side layer in a first part and a second part with said first part extending from said seam towards said longitudinal centre axis and said second part extending from said seam away from said longitudinal centre axis, said first parts extending above said topsheet and being loose therefrom to form said liquid side barriers;
   wherein the side portion of the backsheet is arranged in direct contact with the second part of the side layer from an end of the topsheet to an outer edge of the side flap when the disposable hygiene article is in use.

2. The disposable hygiene article according to claim 1, wherein said side barriers are provided for being at least partly raised to a substantially upright position in use.

3. The disposable hygiene article according to claim 1, wherein said side barriers are provided for being at least partly raised by folding said flexible side flaps to a position in which said hygiene article is secured to said garment.

4. The disposable hygiene article according to claim 1, wherein said side barriers arc provided for being at least partly raised by folding said flexible side flaps substantially along said seams.

5. The disposable hygiene article according to claim 1, wherein on each side of the absorbent core the side layer is attached to the respective side portion of the backsheet.

6. The disposable hygiene article according to claim 5, wherein said attachment is provided along outer edges of the side layer and the respective side portion of the backsheet.

7. The disposable hygiene article according to claim 1, wherein said first part of each of said side layers is formed by a multiple layered section of the respective side layer.

8. The disposable hygiene article according to claim 7, wherein said multiple layered section is formed by at least one fold of said side layer.

9. The disposable hygiene article according to claim 1, wherein said first parts extend over the full length of the article.

10. The disposable hygiene article according to claim 1, wherein said first parts have a width in a transverse direction (T) of the article ranging from 2.0 to 10.0 mm.

11. The disposable hygiene article according to claim 1, wherein the liquid side barriers consist entirely of non-elastic material.

12. The disposable hygiene article according to claim 1, wherein said article further comprises an acquisition layer positioned between said absorbent core and said topsheet.

13. The disposable hygiene article according to claim 1, wherein said seam is obtained by at least one of: welding, such as ultrasonic welding; by applying a chemical compound such as an adhesive; and by applying heat and/or pressure.

14. The disposable hygiene article according to claim 1, wherein a coloured indication is provided on the article to highlight the presence of the liquid side barriers, said coloured indication preferably being provided by a print on the topsheet underneath each of said first parts, said print preferably being provided on a garment facing side of the topsheet.

15. The disposable hygiene article according claim 1, wherein said first parts have a width in a transverse direction (T) of the article ranging from 3.0 to 7.0 mm.

16. The disposable hygiene article according to claim 1, wherein a width of said first part in a transverse direction (T) of the article is greater than a width of said second part in said transverse direction (T) of the article.

* * * * *